(12) United States Patent
Nguyen-Kim et al.

(10) Patent No.: US 8,747,824 B2
(45) Date of Patent: Jun. 10, 2014

(54) COSMETIC PRODUCT COMPRISING AT LEAST ONE WATER-SOLUBLE COPOLYMER WHICH CONTAINS (METH)ACRYLAMIDE UNITS

(75) Inventors: Son Nguyen-Kim, Hemsbach (DE); Peter Hoessel, Schifferstadt (DE); Gabi Mueller, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 2070 days.

(21) Appl. No.: 10/511,594

(22) PCT Filed: May 2, 2003

(86) PCT No.: PCT/EP03/04647
§ 371 (c)(1),
(2), (4) Date: Nov. 2, 2004

(87) PCT Pub. No.: WO03/092640
PCT Pub. Date: Nov. 13, 2003

(65) Prior Publication Data
US 2005/0175572 A1    Aug. 11, 2005

(30) Foreign Application Priority Data
May 3, 2002 (DE) .................. 102 19 889
Sep. 19, 2002 (DE) .................. 102 43 573

(51) Int. Cl.
*A61K 8/81* (2006.01)
(52) U.S. Cl.
USPC ....................................... 424/70.16

(58) Field of Classification Search
USPC ........................................ 424/70.16
See application file for complete search history.

(56) References Cited

U.S. PATENT DOCUMENTS

| | | | | |
|---|---|---|---|---|
| 3,006,900 | A | * | 10/1961 | Hans et al. .................. 526/219.1 |
| 5,773,541 | A | * | 6/1998 | Boeckh et al. ............... 526/209 |
| 5,869,032 | A | * | 2/1999 | Tropsch et al. ............. 424/70.15 |
| 6,174,946 | B1 | * | 1/2001 | Rubenacker et al. ......... 524/244 |
| 6,770,293 | B2 | * | 8/2004 | Angel et al. .................. 424/451 |
| 2001/0026791 | A1 | * | 10/2001 | Lede et al. .................. 424/70.15 |
| 2002/0150542 | A1 | | 10/2002 | Steinmetz et al. |
| 2003/0147929 | A1 | * | 8/2003 | Kim et al. ..................... 424/401 |
| 2008/0033091 | A1 | * | 2/2008 | Bohrer et al. ................ 524/438 |

FOREIGN PATENT DOCUMENTS

| | | | | |
|---|---|---|---|---|
| GB | 1 357 391 | * | 6/1974 | ............. C08F 1/13 |
| GB | 1602420 | | 11/1981 | |
| JP | 53-142544 | | 12/1978 | |
| JP | 8-319319 | | 12/1996 | |
| JP | 10-147509 | | 6/1998 | |
| JP | 2001-513541 | | 9/2001 | |
| JP | 2003-176496 | | 6/2003 | |
| WO | WO 99/09950 | | 3/1999 | |
| WO | WO 01/56536 A1 | | 8/2001 | |

* cited by examiner

*Primary Examiner* — Aradhana Sasan
(74) *Attorney, Agent, or Firm* — Oblon, Spivak, McClelland, Maier & Neustadt, L.L.P.

(57) ABSTRACT

The invention relates to a cosmetic product containing at least one water-soluble copolymer which is obtained by radical copolymerization of acrylamide and/or methacrylamide and other water-soluble a,β-ethylenically unsaturated compounds which are copolymerizable therewith, optionally in the presence of a water-soluble polymeric graft base.

20 Claims, No Drawings

COSMETIC PRODUCT COMPRISING AT LEAST ONE WATER-SOLUBLE COPOLYMER WHICH CONTAINS (METH)ACRYLAMIDE UNITS

The present invention relates to a cosmetic composition which comprises at least one water-soluble copolymer obtainable by free-radical copolymerization of acrylamide and/or methacrylamide and further water-soluble α,β-ethylenically unsaturated compounds copolymerizable therewith, optionally in the presence of a water-soluble polymeric graft base.

Cosmetically and pharmaceutically acceptable water-soluble polymers are used widely in cosmetics and medicine. In soaps, creams and lotions, for example, they are usually used as formulating agents, e.g. as thickener, foam stabilizer or water absorbent or else to alleviate the irritative effect of other ingredients or to improve the dermal application of active ingredients. Their aim in hair cosmetics is to influence the properties of the hair. In pharmacy, they are used, for example, as coatings or binders for solid medicaments.

For hair cosmetics, film-forming polymers are, for example, used as conditioners for improving the dry and wet combability, feel to the touch, shine and appearance, and for imparting antistatic properties to the hair. Preference is given to using water-soluble polymers with polar, frequently cationic, functionalities which have a greater affinity to the surface of the hair which is negatively charged as a result of its structure. The structure and mode of action of various hair-treatment polymers are described in Cosmetic & Toiletries 103 (1988) 23. Commercially available conditioner polymers are, for example, cationic hydroxyethylcellulose, cationic polymers based on N-vinylpyrrolidone, e.g. copolymers of N-vinylpyrrolidone and quaternized N-vinylimidazole, acrylamide and diallyldimethylammonium chloride or silicones.

To set hairstyles, for example, use is made of vinyllactam homo- and copolymers and carboxylate-containing polymers. Requirements for hair-setting resins are, for example, strong hold at high atmospheric humidity, elasticity, ability to be washed out of the hair, compatibility in the formulation and a pleasant feel of the hair treated therewith.

The provision of products with a complex profile of properties often presents problems. For example, there is a need for polymers for cosmetic compositions which are able to form essentially smooth, tack-free films which give the hair and the skin a pleasant feel and at the same time have a good conditioning effect or setting action. In addition, esthetic requirements are increasingly placed by the consumer on cosmetic and pharmaceutical products. For example, in the case of such products, a preference for clear, opaque formulations in the form of gels is currently being observed.

DE-C-963 057 describes polymers based on vinylimidazoles which can contain further copolymerized comonomers. Suitable comonomers mentioned are, inter alia, vinylpyrrolidone, vinylcaprolactam and acrylamide.

U.S. Pat. No. 3,269,969 describes the preparation of dispersants by heat treatment of (meth)acrylamide copolymers in the presence of water. In this process, an increase in the K value coupled with an improvement in the water solubility is achieved. The copolymers used can contain a large number of further monomers in incorporated form, with vinyllactams and (meth)acrylamides, inter alia, being specified.

DE-B-1 006 151 describes the process for the preparation of homopolymers and copolymers from unsaturated carboxamides. Suitable comonomers which are specified are, inter alia, unsaturated carboxamides and vinyllactams.

DE-B-1 090 079 describes the use of aqueous polymer dispersions which contain copolymers with a high content of unsaturated carboxamides as auxiliaries for paper finishing.

A use of the abovementioned polymers in cosmetics is not described.

U.S. Pat. No. 5,478,553 and U.S. Pat. No. 5,632,977 describe hair-setting compositions which comprise homo- or copolymers of N-vinylformamide. A suitable comonomer mentioned is, inter alia, also acrylamide.

U.S. Pat. No. 5,334,287 discloses graft polymers obtainable by free-radically initiated polymerization of N-vinylcarboxamides, preferably N-vinylformamide, and optionally other monomers in the presence of monosaccharides, oligosaccharides and polysaccharides. Additional monomers which are mentioned are also acrylamide and methacrylamide, in addition to a large number of others. A suitability of these graft copolymers as active ingredient in cosmetic formulations is not mentioned.

WO 02/15854 describes the use of graft copolymers obtainable by free-radical graft copolymerization of at least one open-chain N-vinylamide compound and optionally at least one other monomer copolymerizable therewith on a polymeric graft base for cosmetic applications.

It is an object of the present invention to provide cosmetic and pharmaceutical compositions with good performance properties. They should be capable of forming tack-free smooth films. In particular, they should have a good setting action and be suitable for the preparation of products in the form of gels.

We have found that this object is achieved by a cosmetic composition which comprises at least one water-soluble copolymer obtainable by free-radical copolymerization of acrylamide and/or methacrylamide and further water-soluble α,β-ethylenically unsaturated compounds copolymerizable therewith, optionally in the presence of a water-soluble polymeric graft base.

The invention therefore provides a cosmetic or pharmaceutical composition comprising
A) at least one water-soluble or water-dispersible copolymer obtainable by free-radical copolymerization of
  a) 5 to 90% by weight, based on the total weight of components a) to d), of acrylamide and/or methacrylamide,
  b) 0 to 85% by weight, based on the total weight of components a) to d), of at least one α,β-ethylenically unsaturated amide-containing compound of the formula I

where
$R^1$ is a group of the formula $CH_2=CR^4-$ where $R^4=H$ or $C_1$-$C_4$-alkyl, and $R^2$ and $R^3$, independently of one another, are each H, alkyl, cycloalkyl, heterocycloalkyl, aryl or hetaryl, with the proviso that one of the radicals $R^2$ and $R^3$ is different from H, or $R^2$ and $R^3$ together with the nitrogen atom to which they are bonded are a five- to eight-membered heterocycle,
or $R^2$ is a group of the formula $CH_2=CR^4-$ and $R^1$ and $R^3$, independently of one another, are each H, alkyl, cycloalkyl, heterocycloalkyl, aryl or hetaryl, or $R^1$ and $R^3$ together with the amide group to which they are bonded are a lactam with 5 to 8 ring atoms, c) 0 to 40% by weight, based on the total weight of components a) to d), of at least one unsaturated water-soluble compound which is different from components a) and b) and copolymerizable therewith, where the proportion by weight of the sum of components b) and c) is at least 5% by weight, optionally in the presence of up to 25% by weight, based on the total weight of components a) to d), of at least one water-soluble component d), which is chosen from d1) polyether-containing compounds, d2) polymers which have at least 50% by weight repeat units derived from vinyl alcohol, d3) starch and starch derivatives, and mixtures thereof, and B) at least one cosmetically acceptable carrier.

For the purposes of the present invention, the expression "alkyl", includes straight-chain and branched alkyl groups. Suitable short-chain alkyl groups are, for example, straight-chain or branched $C_1$-$C_7$-alkyl, preferably $C_1$-$C_6$-alkyl and particularly preferably $C_1$-$C_4$-alkyl, groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

Suitable longer-chain $C_8$-$C_{30}$-alkyl or $C_8$-$C_{30}$-alkenyl groups are straight-chain and branched alkyl or alkenyl groups. These are preferably predominantly linear alkyl radicals, as also arise in natural or synthetic fatty acids and fatty alcohols and also oxo alcohols which may additionally be mono-, di- or polyunsaturated. These include, for example, n-hexyl(ene), n-heptyl(ene), n-octyl(ene), n-nonyl(ene), n-decyl(ene), n-undecyl(ene), n-dodecyl(ene), n-tridecyl (ene), n-tetradecyl(ene), n-pentadecyl(ene), n-hexadecyl (ene), n-heptadecyl(ene), n-octadecyl(ene) and n-nonadecyl (ene) etc.

Cycloalkyl is preferably $C_5$-$C_8$-cycloalkyl, such as cyclopentyl, cyclohexyl, cycloheptyl or cyclooctyl.

For the purposes of the present invention, the term "heterocycloalkyl" includes saturated, cycloaliphatic groups with, in general, 4 to 7, preferably 5 or 6, ring atoms in which 1 or 2 of the ring carbon atoms are replaced by heteroatoms chosen from the elements oxygen, nitrogen and sulfur and which may optionally be substituted where, in the case of a substitution, these heterocycloaliphatic groups may carry 1, 2 or 3, preferably 1 or 2, particularly preferably 1, substituent chosen from alkyl, aryl, $COOR^a$, $COO^-M^+$ and $NE^1E^2$, preferably alkyl. Examples of such heterocycloaliphatic groups which may be mentioned are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

Aryl includes unsubstituted and substituted aryl groups and is preferably phenyl, tolyl, xylyl, mesityl, naphthyl, fluorenyl, anthracenyl, phenanthrenyl, naphthacenyl and in particular is phenyl, tolyl, xylyl or mesityl.

Substituted aryl radicals preferably have 1, 2, 3, 4 or 5, in particular 1, 2 or 3, substituents chosen from alkyl, alkoxy, carboxyl, carboxylate, trifluoromethyl, —$SO_3H$, sulfonate, $NE^1E^2$, alkylene-$NE^1E^2$, nitro, cyano or halogen.

Hetaryl is preferably pyrrolyl, pyrazolyl, imidazolyl, indolyl, carbazolyl, pyridyl, quinolinyl, acridinyl, pyridazinyl, pyrimidinyl or pyrazinyl.

In the text below, compounds which may be derived from acrylic acid and methacrylic acid are sometimes referred to in abbreviated form by adding the syllable "(meth)" to the compound derived from acrylic acid.

The compositions according to the invention can advantageously be formulated as gels under standard conditions (20° C.). "Gel-like consistency" is shown by compositions which have a higher viscosity than a liquid and which are self-supporting, i.e. they retain a shape given to them without a shape-stabilizing coating. In contrast to solid formulations, however, gel-like formulations can be readily deformed under the application of shear forces. The viscosity of the gel-like compositions is preferably in a range greater than 600 to about 60 000 mPas. The gels are preferably hair gels, these having a viscosity of preferably 6000 to 30 000 mPas.

For the purposes of the present invention, water-soluble monomers and polymers are understood as meaning monomers and polymers which dissolve in water to at least 1 g/l at 20° C. Water-dispersible polymers are understood as meaning polymers which disintegrate into dispersible particles under the application of shear forces, for example by stirring.

The copolymers A) used according to the invention and for the preparation of the cosmetic compositions according to the invention preferably do not contain any copolymerized acid-containing monomers.

If the free-radical copolymerization of components a) and optionally b) and/or c) is carried out in the presence of at least one compound of component d), copolymers A) with advantageous properties are obtained. This may, for example, result from an at least partial grafting onto component d) as graft base. However, mechanisms other than grafting are also conceivable. Component A) includes very generally the process products of free-radical copolymerization which are understood as e.g. pure graft polymers, mixtures of graft polymers with ungrafted compounds of component d), homo- and copolymers of monomers a) and optionally b) and/or c), and any mixtures. Fractions of ungrafted compounds of component d) may be advantageous, depending on the intended use of the copolymers A). They may, for example, assume an effect as emulsifier or protective colloid.

The copolymer A) comprises 5 to 90% by weight, preferably 10 to 85% by weight, particularly preferably 15 to 80% by weight, based on the total weight of components a) to d), of acrylamide and/or methacrylamide in copolymerized form.

According to a preferred embodiment, the copolymer A) comprises 5 to 85% by weight, particularly preferably 10 to 80% by weight, of at least one compound of component b) in copolymerized form.

The compounds of component b) are preferably chosen from N-vinyllactams, N-vinylamides of saturated monocarboxylic acids, N-alkyl- and N,N-dialkylamides of α,β-ethylenically unsaturated monocarboxylic acids and mixtures thereof.

Preferred monomers b) are N-vinyllactams and derivatives thereof which, for example, may have one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam and N-vinyl-7-ethyl-2-caprolactam etc. Preference is given to using N-vinylpyrrolidone and N-vinylcaprolactam.

N-Vinylamides suitable as monomers b) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide, N-vinylbutyramide and mixtures thereof. Preference is given to using N-vinylformamide.

N-Alkyl- and N,N-dialkylamides of α,β-ethylenically unsaturated monocarboxylic acids suitable as monomers b) are, for example, N-methyl(meth)acrylamide, N-ethyl(meth)acrylamide, N-propyl(meth)acrylamide, N-tert-butyl(meth)acrylamide, N,N-dimethyl(meth)acrylamide, N,N-diethyl(meth)acrylamide, etc.

The monomers b) specified above may be used individually and in the form of mixtures.

According to a preferred embodiment, the copolymer A) comprises 3 to 30% by weight, particularly preferably 5 to 25% by weight, of at least one compound of component c) in copolymerized form.

Preferably, the compounds of component c) are chosen from α,β-ethylenically unsaturated water-soluble compounds with nonionic, cationogenic and cationic hydrophilic groups.

The cationogenic and/or cationic groups of component c) are preferably nitrogen-containing groups, such as primary, secondary and tertiary amino groups and quaternary ammonium groups. The nitrogen-containing groups are preferably tertiary amino groups or quaternary ammonium groups. Charged cationic groups can be generated from the amine nitrogens either by protonation, e.g. with carboxylic acids, such as lactic acid, or mineral acids, such as phosphoric acid, sulfuric acid and hydrochloric acid, or by quaternization, e.g. with alkylating agents, such as $C_1$-$C_4$-alkyl halides or sulfates. Examples of such alkylating agents are ethyl chloride, ethyl bromide, methyl chloride, methyl bromide, dimethyl sulfate and diethyl sulfate. A protonation or quaternization can generally be carried out either before or after the polymerization.

Suitable compounds c) are, for example, the esters of α,β-ethylenically unsaturated mono- and dicarboxylic acids with aminoalcohols, preferably $C_2$-$C_{12}$-aminoalcohols. These may preferably be $C_1$-$C_8$-monoalkylated or -dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof. Preference is given to using tert-butylaminoethyl(meth)acrylate, N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate, N,N-dimethylaminocyclohexyl(meth)acrylate etc. Preference is given to using N,N-dimethylaminoethyl(meth)acrylate and N,N-dimethylaminopropyl(meth)acrylate.

Esters of vinyl alcohol with monocarboxylic acids suitable as monomers c) are, for example, vinyl formate, vinyl acetate and vinyl propionate.

Vinyl- and allyl-substituted heteroaromatic compounds suitable as monomers c) are, for example, N-vinylimidazole and derivatives thereof, such as N-vinyl-2-methylimidazole etc.

Suitable monomers c) are also allylamines and allylammonium salts, such as diallylamine, diallylmethylamine and diallyldimethylammonium chloride.

Suitable monomers c) are also the amides of the abovementioned α,β-ethylenically unsaturated mono- and dicarboxylic acids with diamines which have a tertiary and a primary or secondary amino group. These include, for example, N-[2-(dimethylamino)ethyl]-acrylamide, N-[2-(dimethylamino)ethyl]methacrylamide, N-[3-(dimethylamino)propyl]acrylamide, N-[3-(dimethylamino)-propyl]methacrylamide, N-[4-(dimethylamino)butyl]acrylamide, N-[4-(dimethylamino)butyl]methacrylamide, N-[2-(diethylamino)-ethyl]acrylamide, N-[4-(dimethylamino)cyclohexyl]acrylamide, N-[4-(dimethylamino)cyclohexyl]methacrylamide etc. Preference is given to using N-[3-(dimethylamino)propyl]acrylamide, N-[3-(dimethylamino)propyl]methacrylamide.

Suitable monomers c) are also polyether acrylates, which for the purposes of this invention are generally understood as meaning esters of α,β-ethylenically unsaturated mono- and dicarboxylic acids with polyetherols. Suitable polyetherols are linear or branched substances having terminal hydroxyl groups which contain ether bonds. They generally have a molecular weight in the range from about 150 to 20 000. Suitable polyetherols are polyalkylene glycols, such as polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers may contain the copolymerized alkylene oxide units in random distribution or in the form of blocks. Preference is given to ethylene oxide/propylene oxide copolymers. Preferred as component c) are polyether acrylates of the general formula II

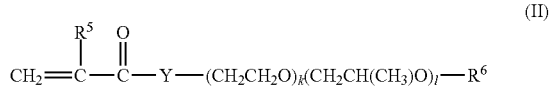

in which
the order of the alkylene oxide units is arbitrary,
k and l, independently of one another, are each an integer from 0 to 500, where the sum of k and l is at least 5,
$R^5$ is hydrogen or $C_1$-$C_8$-alkyl, and
$R^6$ is hydrogen or $C_1$-$C_{18}$-alkyl,
Y is O or $NR^7$, where $R^7$ is hydrogen, $C_1$-$C_8$-alkyl or $C_5$-$C_8$-cycloalkyl.

Preferably, k is an integer from 1 to 500, in particular 3 to 250. l is preferably an integer from 0 to 100.

Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl.

$R^6$ in the formula II is preferably hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Y in the formula II is preferably O or NH.

Suitable polyether acrylates c) are e.g. the polycondensation products of the abovementioned α,β-ethylenically unsaturated mono- and/or dicarboxylic acids and their acid chlorides, amides and anhydrides with polyetherols. Suitable polyetherols may be readily prepared by reaction of ethylene oxide, 1,2-propylene oxide and/or epichlorohydrin with a starter molecule, such as water or a short-chain alcohol $R^6$—OH. The alkylene oxides may be used individually, alternately one after the other or as a mixture. The polyether acrylates c) can be used alone or in mixtures for the preparation of the polymers used according to the invention.

Suitable polyether acrylates are also urethane (meth)acrylates with alkylene oxide groups. Such compounds are described in DE 198 38 851 (component e2)), to which reference is hereby made in its entirety.

The copolymers A) can, if desired, contain at least one crosslinker, i.e. a compound with 2 or more than 2 ethylenically unsaturated double bonds, in copolymerized form. Preference is given to using crosslinkers in an amount of from 0.01 to 10% by weight, particularly preferably 0.1 to 3% by weight, based on the total weight of components a) to d)).

Crosslinking monomers which can be used are compounds with at least two ethylenically unsaturated double bonds, such as, for example, esters of ethylenically unsaturated carboxylic acids, such as acrylic acid or methacrylic acid and polyhydric alcohols, ethers of at least dihydric alcohols, such as, for example, vinyl ethers or allyl ethers.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis (hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans with molecular weights of in each case 200 to 10 000. Apart from the homopolymers of ethylene oxide or propylene oxide, it is also possible to use block copolymers of ethylene oxide or propylene oxide or copolymers which contain ethylene oxide and propylene oxide groups in incorporated form. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose and mannose. It is, of course, also possible to use the polyhydric alcohols following reaction with ethylene oxide or propylene oxide as the corresponding ethoxylates or propoxylates, respectively. The polyhydric alcohols may also firstly be converted into the corresponding glycidyl ethers by reaction with epichlorohydrin.

Further suitable crosslinkers are the vinyl esters or the esters of monohydric, unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric, unsaturated alcohols with polyhydric carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example oleic acid, crotonic acid, cinnamic acid or 10-undecenoic acid.

Also suitable are straight-chain or branched, linear or cyclic aliphatic or aromatic hydrocarbons which have at least two double bonds which, in the case of the aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes having molecular weights of from 200 to 20 000.

Also suitable are amides of unsaturated carboxylic acids, such as, for example, acrylic and methacrylic acid, itaconic acid, maleic acid, and N-allylamines of at least dihydric amines, such as, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dihydric carboxylic acids, as described above.

Further suitable crosslinkers are triallylamine or corresponding ammonium salts, e.g. triallylmethylammonium chloride or methylsulfate.

In addition, N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea may be used.

Further suitable crosslinkers are divinyldioxane, tetraallylsilane or tetravinylsilane.

Particularly preferred crosslinkers are, for example, methylenebisacrylamide, divinylbenzene, triallylamine and triallylammonium salts, divinylimidazole, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and allyl or vinyl ethers of polyhydric alcohols, for example 1,2-ethanediol, 1,4-butanediol, diethylene glycol, trimethylolpropane, glycerol, pentaerythritol, sorbitan and sugars, such as sucrose, glucose, mannose.

Particularly preferred crosslinkers are pentaerythritol triallyl ether, allyl ethers of sugars, such as sucrose, glucose, mannose, divinylbenzene, N,N'-methylenebisacrylamide, N,N'-divinylethyleneurea, and (meth)acrylic esters of glycol, butanediol, trimethylolpropane or glycerol or (meth)acrylic esters of glycol, butanediol, trimethylolpropane or glycerol reacted with ethylene oxide and/or epichlorohydrin. Very particular preference is given to N,N'-methylenebisacrylamide, diallyltartardiamide, diallyl phthalate, diallylurea, glycol di(meth)acrylate, allyl(meth)acrylate, and polyallyl ether.

According to a suitable embodiment, the copolymerization for the preparation of the copolymers A) takes place in the presence of at least one compound of component d).

In a preferred embodiment, the amount of component d) used is 1 to 25% by weight, particularly preferably 3 to 20% by weight, based on the total weight of components a) to d).

The compounds of component d) used according to the invention essentially do not contain any carbon-carbon double bonds. According to a suitable embodiment, the compounds of component d) do not contain any silicon atom-containing groups.

Suitable polyether-containing compounds d1) are generally water-soluble or water-dispersible nonionic polymers which have polyalkylene glycol groups. The proportion of polyalkylene glycol groups is preferably at least 40% by weight, based on the total weight of the compound d1). Polyether-containing compounds d1) which may be used are, for example, the abovementioned polyalkylene glycols, polyesters based on polyalkylene glycols and polyether urethanes.

Depending on the nature of the monomer building blocks used for their preparation, the polyether-containing compounds d1) contain the following structural units:

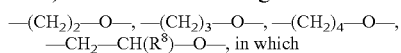

$R^8$ is $C_1$-$C_{24}$-alkyl, preferably $C_1$-$C_4$-alkyl.

The compounds d1) can additionally have bridging groups which are chosen, for example, from:

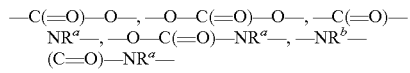

in which $R^a$ and $R^b$, independently of one another, are each hydrogen, $C_1$-$C_{30}$-alkyl, preferably $C_1$-$C_4$-alkyl or cycloalkyl.

As polyether d1), preference is given to using polymers of the formula III with a molecular weight of >300

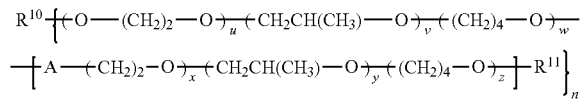

(III)

in which the variables, independently of one another, have the following meanings:
$R^{10}$ is hydrogen, $C_1$-$C_{24}$-alkyl, $R^8$—C(=O)—, $R^8$—NH—C(=O)—, polyalcohol radical;
$R^{11}$ is hydrogen, $C_1$-$C_{24}$-alkyl, $R^8$—C(=O)—, $R^8$—NH—C(=O)—;
$R^8$ is $C_1$-$C_{24}$-alkyl;
A is —C(=O)—O, —C(=O)—B—C(=O)—O, —C(=O)—NH—B—NH—C(=O)—O;
B is —(CH$_2$)$_t$—, optionally substituted cycloalkylene, hetero-cycloalkylene or arylene;
n is 1 to 200, preferably 1 to 100;
s is 0 to 1000, preferably 0 to 100;
t is 2 to 12, preferably 2 to 6;
u is 1 to 1000, preferably 1 to 500;
v is 0 to 1000, preferably 1 to 500;
w is 0 to 1000, preferably 1 to 500;
x is 0 to 1000, preferably 1 to 500;
y is 0 to 1000, preferably 1 to 500;
z is 0 to 1000, preferably 1 to 500.

The terminal primary hydroxyl groups of the polyethers prepared on the basis of polyalkylene oxides, and the secondary OH groups of polyglycerol may here be present either freely in unprotected form, or may be etherified or esterified with alcohols of chain length $C_1$-$C_{24}$ or with carboxylic acids of chain length $C_1$-$C_{24}$, respectively, or may be reacted with isocyanates to give urethanes. Preference is given to using polyether urethanes.

Preferred representatives of the abovementioned alkyl radicals which may be mentioned are branched or unbranched $C_1$-$C_{12}$-, particularly preferably $C_1$-$C_6$-alkyl chains.

The molecular weight of the polyethers is in the range greater than 300 (number-average), preferably in the range from 300 to 100 000, particularly preferably in the range from 500 to 50 000, very particularly preferably in the range from 800 to 40 000.

Advantageously, homopolymers of ethylene oxide or copolymers with an ethylene oxide fraction of from 40 to 99% by weight are used. For the ethylene oxide polymers which are preferably to be used, the proportion of copolymerized ethylene oxide is thus 40 to 100 mol %. Suitable comonomers for these copolymers are propylene oxide, butylene oxide and/or isobutylene oxide. Suitable are, for example, copolymers of ethylene oxide and propylene oxide, copolymers of ethylene oxide and butylene oxide, and copolymers of ethylene oxide, propylene oxide and at least one butylene oxide. The ethylene oxide fraction of the copolymers is preferably 40 to 99 mol %, the propylene oxide fraction is 1 to 60 mol % and the fraction of butylene oxide in the copolymers is 1 to 30 mol %. In addition to straight-chain homo- or copolymers, it is also possible to use branched homo- or copolymers as polyether-containing compounds d1).

Branched polymers may be prepared by adding ethylene oxide and optionally also propylene oxide and/or butylene oxides onto polyalcohol radicals, e.g. onto pentaerythritol, glycerol or onto sugar alcohols, such as D-sorbitol and D-mannitol, but also onto polysaccharides, such as cellulose and starch. The alkylene oxide units may be present within the polymer in randomly distributed form or in the form of blocks.

It is, however, also possible to use polyesters of polyalkylene oxides and aliphatic or aromatic dicarboxylic acids, e.g. oxalic acid, succinic acid, adipic acid and terephthalic acid with molar masses of from 1500 to 25 000, as are described, for example, in EP-A-0 743 962, as polyether-containing compound. In addition, it is also possible to use polycarbonates by reacting polyalkylene oxides with phosgene or carbonates, such as, for example, diphenyl carbonate, and also polyurethanes by reacting polyalkylene oxides with aliphatic and aromatic diisocyanates.

According to a preferred embodiment, for the preparation of the copolymers A), a component d1) is used which includes at least one polyether urethane.

Suitable polyether urethanes are the condensation products of polyether polyols, such as polyetherdiols, with polyisocyanates, such as diisocyanates. Suitable polyether polyols are the abovementioned polyalkylene glycols which are obtainable, for example, from the polymerization of cyclic ethers, such as tetrahydrofuran, or from the reaction of one or more alkylene oxides with a starter molecule which has two or more active hydrogen atoms.

Suitable polyisocyanates are chosen from compounds with 2 to 5 isocyanate groups, isocyanate prepolymers with an average number of from 2 to 5 isocyanate groups, and mixtures thereof. These include, for example, aliphatic, cycloaliphatic and aromatic di-, tri- and polyisocyanates. Suitable diisocyanates are, for example, tetramethylene diisocyanate, hexamethylene diisocyanate, 2,3,3-trimethylhexamethylene diisocyanate, 1,4-cyclohexylene diisocyanate, isophorone diisocyanate, 1,4-phenylene diisocyanate, 2,4- and 2,6-tolylene diisocyanate and isomeric mixtures thereof (e.g. 80% 2,4- and 20% 2,6-isomer), 1,5-naphthylene diisocyanate, 2,4- and 4,4'-diphenylmethane diisocyanate. A suitable triisocyanate is e.g. triphenylmethane 4,4',4"-triisocyanate. Also suitable are isocyanate prepolymers and polyisocyanates which are obtainable by addition of the abovementioned isocyanates onto polyfunctional hydroxyl- or amine-containing compounds. Also suitable are polyisocyanates which form by biuret or isocyanurate formation. Preference is given to using hexamethylene diisocyanate, trimerized hexamethylene diisocyanate, isophorone diisocyanate, 2,4-tolylene diisocyanate, 2,6-tolylene diisocyanate, and mixtures thereof.

Suitable graft bases are also preferably polymers d2) which have at least 50% by weight of vinyl alcohol units. These polymers preferably contain at least 70% by weight, very particularly preferably 80% by weight, of polyvinyl alcohol units. Such polymers are usually prepared by polymerization of a vinyl ester and subsequent at least partial alcoholysis, aminolysis or hydrolysis. Preference is given to vinyl esters of linear and branched $C_1$-$C_{12}$-carboxylic acids, and very particular preference is given to vinyl acetate. The vinyl esters may of course also be used in a mixture.

Suitable comonomers of the vinyl ester for the synthesis of the graft base d2) are, for example, N-vinylcaprolactam, N-vinylpyrrolidone, N-vinylimidazole, N-vinyl-2-methylimidazole, N-vinyl-4-methylimidazole, 3-methyl-1-vinylimidazolium chloride, 3-methyl-1-vinylimidazolium methylsulfate, diallylammonium chloride, styrene, alkylstyrenes.

Further suitable comonomers for the preparation of the graft base d2) are, for example, monoethylenically unsaturated $C_3$-$C_6$-carboxylic acids, such as, for example, acrylic acid, methacrylic acid, crotonic acid, fumaric acid, and the esters, amides and nitriles thereof, such as, for example, methyl acrylate, ethyl acrylate, methyl methacrylate, ethyl methacrylate, stearyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, maleic anhydride and its half-esteer, alkylene glycol (meth) acrylates, acrylamide, methacrylamide, N-dimethylacrylamide, N-tert-butylacrylamide, acrylonitrile, methacrylonitrile, vinyl ethers, such as, for example, methyl, ethyl, butyl or dodecyl vinyl ether, cationic monomers, such as dialkylaminoalkyl(meth)acrylates and dialkylaminoalkyl(meth)acrylamides, such as dimethylaminoethyl acrylate, diethylaminoethyl acrylate, diethylaminoethyl methacrylate, and the salts of the last-mentioned monomers with carboxylic acids or mineral acids and the quaternized products.

Preferred graft bases d2) are polymers which are prepared by homopolymerization of vinyl acetate and subsequent at least partial hydrolysis, alcoholysis or aminolysis.

The graft base d2) is prepared by known processes, for example solution, precipitation, suspension or emulsion polymerization using compounds which form free radicals under polymerization conditions. The polymerization temperatures are usually in the range from 30 to 200° C., preferably 40 to 110° C. Suitable initiators are, for example, azo and peroxy compounds, and the customary redox initiator systems, such as combinations of hydrogen peroxide and reducing compounds, for example sodium sulfite, sodium bisulfite, sodium formaldehyde sulfoxylate and hydrazine. These systems may optionally additionally also comprise small amounts of a heavy metal salt.

To prepare the graft base d2), the ester groups of the original monomers and optionally of further monomers are at least partially cleaved following polymerization by hydrolysis, alcoholysis or aminolysis. In the text below, this process step is generally referred to as saponification. The saponification takes place in a manner known per se by adding a base or acid, preferably by adding a sodium hydroxide or potassium hydroxide solution in water and/or alcohol. Particular preference is given to using methanolic sodium hydroxide or potassium hydroxide solutions. The saponification is carried out at temperatures in the range from 10 to 80° C., preferably in the range from 20 to 60° C. The degree of saponification depends on the amount of base or acid used, on the saponification temperature, the saponification time and the water content of the solution.

Particularly preferred graft bases d2) are polymers which are prepared by homopolymerization of vinyl acetate and subsequent at least partial saponification. Such polymers containing polyvinyl alcohol units are available under the name Mowiol®.

As component d), preference is given to using starch and/or starch derivatives d3). These include substances which contain saccharide structures. Such natural substances are, for example, saccharides of vegetable or animal origin or products which are formed as a result of the metabolization by microorganisms, and degradation products thereof. Suitable graft bases d3) are, for example, oligosaccharides, polysaccharides, oxidatively, enzymatically or hydrolytically degraded polysaccharides, oxidatively hydrolytically degraded or oxidatively enzymatically degraded polysaccharides, chemically modified oligo- or 9 polysaccharides and mixtures thereof. Preferred products are the compounds given in U.S. Pat. No. 5,334,287 in column 4, line 20 to column 5, line 45.

Suitable commercially available products are the C-Pur® and C-Dry® grades from Cerestar.

If desired, mixtures of compounds of component d) can be used. Advantageous mixtures are, for example, those which contain at least one compound d2) and at least one compound d3).

The copolymer A) according to the invention and, in a first embodiment, used in the compositions according to the invention is preferably obtainable by free-radical copolymerization of a) 10 to 45% by weight, based on the total weight of components a) to d), of methacrylamide, b) 60 to 90% by weight, based on the total weight of components a) to d), of vinylpyrrolidone and/or vinylcaprolactam, c) 0 to 25% by weight, based on the total weight of components a) to d), of at least one unsaturated water-soluble compound which is different from a) and b) and is copolymerizable therewith, optionally in the presence of up to 20% by weight, based on the total weight of components a) to d), of polymers d2) and/or starch and starch derivatives d3).

Particularly preferably, the copolymer A) is obtainable by free-radical polymerization of a) 20 to 40% by weight of methacrylamide, b) 40 to 70% by weight of vinylpyrrolidone, in the presence of from 1 to 20% by weight of polymers d2) and/or starch and starch derivatives d3).

The copolymer A) is also particularly preferably obtainable by free-radical polymerization of a) 30 to 40% by weight of methacrylamide, b) 20 to 60% by weight of vinylpyrrolidone and 1 to 20% by weight of vinylcaprolactam.

The copolymer A) is also preferably obtainable by free-radical polymerization of a) 20 to 40% by weight of methacrylamide, b) 40 to 70% by weight of vinylpyrrolidone and c) 1 to 20% by weight of at least one water-soluble compound different from a) and b) and copolymerizable therewith.

In a second embodiment, the copolymer A) according to the invention and used in the compositions according to the invention is preferably obtainable by free-radical copolymerization of a) 5 to 50% by weight, based on the total weight of components a) to d), of methacrylamide, b) 40 to 85% by weight, based on the total weight of components a) to d), of at least one compound chosen from vinylpyrrolidone, vinylcaprolactam, N,N-dimethylacrylamide and mixtures thereof, c) 0.2 to 20% by weight, based on the total weight of components a) to d), of at least one unsaturated water-soluble compound which is different from a) and b) and is copolymerizable therewith and is chosen from vinylimidazole and derivatives thereof, polyether acrylates and mixtures thereof, optionally in the presence of up to 10% by weight, based on the total weight of components a) to d), of polymers d2) which are derived from vinyl alcohol, and optionally in the presence of up to 1% by weight, based on the total weight of components a) to d), of at least one crosslinker.

Furthermore, the copolymer A) is preferably obtainable by free-radical polymerization of
a) 7 to 45% by weight of methacrylamide,
b) 50 to 80% by weight of at least one compound chosen from vinylpyrrolidone, vinylcaprolactam, N,N-dimethylacrylamide and mixtures thereof,
c) 0.3 to 10% by weight of at least one compound which is chosen from vinylimidazole and derivatives thereof, polyether acrylates and mixtures thereof,
in the presence of from 0.1 to 10% by weight of polymers d2) which are derived from vinyl alcohol.

The copolymer A) is particularly preferably obtainable by free-radical polymerization of
a) 10 to 45% by weight, preferably 10 to 43% by weight, of methacrylamide,
b) 50 to 80% by weight of vinylpyrrolidone and vinylcaprolactam and
c) 0.3 to 10% by weight of vinylimidazole and/or a derivative thereof.

Furthermore, the copolymer A) is preferably obtainable by free-radical polymerization of
a) 10 to 45% by weight, preferably 20 to 45% by weight, particularly preferably 20 to 43% by weight, and in particular 30 to 40% by weight, of methacrylamide,
b) 50 to 80% by weight, preferably 55 to 70% by weight, of vinylpyrrolidone and
c) 0.5 to 5% by weight, preferably 1 to 4% by weight, of vinylimidazole.

The copolymers A) are prepared by customary processes known to the person skilled in the art, preferably by solution polymerization.

The polymerization temperatures are preferably in a range from about 30 to 120° C., particularly preferably 40 to 100° C. The polymerization is usually carried out under atmospheric pressure, but it can also be carried out under reduced or elevated pressure. A suitable pressure range is between 1 and 5 bar.

To prepare the polymers, the monomers can be polymerized optionally in the presence of component d) either using initiators which form free radicals, or by the action of high-energy radiation, which is understood as also meaning the action of high-energy electrons.

Initiators which can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-toloyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane)dihydrochloride or 2-2'-azobis-(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate.

The polymerization can also be carried out through the action of ultraviolet radiation, optionally in the presence of UV initiators. For the polymerization under the action of UV rays, the photoinitiators or sensitizers which are customarily suitable for this purpose are used. These are, for example, compounds such as benzoin and benzoin ether, α-methylbenzoin or α-phenylbenzoin. It is also possible to use "triplet sensitizers", such as benzyl diketals. The UV radiation sources used are, for example, in addition to high-energy UV lamps, such as carbon arc lamps, mercury vapor lamps or xenon lamps, also low-UV light sources, such as fluorescent tubes with a high blue component.

The amounts of initiator or initiator mixtures used, based on monomers used, are generally between 0.01 and 10% by weight, preferably between 0.1 and 5% by weight.

The polymerization can, for example, be carried out without a diluent. In the case of bulk polymerization using a graft base d), said graft base can be dissolved in at least one monomer and possibly further comonomers and, following the addition of a polymerization initiator, the mixture can be fully polymerized. The polymerization can also be carried out semicontinuously by firstly introducing some, e.g. 10%, of the mixture of graft base d), at least one monomer of group a), possibly further comonomers and initiator to be polymerized, heating the mixture to the polymerization temperature and, after the onset of polymerization, adding the remainder of the mixture to be polymerized in accordance with the progress of the polymerization. The polymers can also be obtained by initially introducing the graft base d) into a reactor, heating it to the polymerization temperature and adding at least one monomer of group a), possibly further comonomers and polymerization initiator either in one portion, batchwise or, preferably, continuously, and polymerizing the mixture.

The polymerization is preferably carried out in a solvent. Suitable solvents are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, glycerol and dioxane. Particular preference is given to the polymerization in water or a water/alcohol mixture, for example in a water/ethanol mixture. The ratio of alcohol to water in such mixtures is preferably in a range from 1:1 to 1:7% by volume.

To adjust the molecular weight, the polymerization can be carried out in the presence of at least one regulator. Regulators which can be used are the customary compounds known to the person skilled in the art, such as, for example, sulfur compounds, e.g. mercaptoethanol, 2-ethylhexyl thioglycolate, thioglycolic acid or dodecyl mercaptan, and tribromochloromethane or other compounds which have a regulating effect on the molecular weight of the resulting polymers. Preference is given to using silicone-free regulators.

To achieve the purest possible polymers with a low residual monomer content, an after-polymerization step can follow the polymerization (main polymerization). The after-polymerization can take place in the presence of the same initiator system as the main polymerization, or a different initiator system. Preferably, the after-polymerization takes place at least at the same, preferably at a higher temperature, than the main polymerization. The temperature during the main polymerization and the after-polymerization is preferably at most 90° C.

In addition, to achieve the purest possible polymers with a low residual monomer content, the polymerization is preferably carried out at a pH in the range from 6 to 8, particularly preferably from 6.4 to 7.4 in order to remove any ammonia which may form under the polymerization conditions and may react with monomers to give undesired by-products. The pH is adjusted by adding a suitable acid, such as lactic acid.

Products with particularly high purity and correspondingly advantageous properties to be used in cosmetics can be achieved if the reaction product is subjected to steam distillation or stripping with steam after the polymerization, if appropriate before and/or after an after-polymerization. This steam treatment also essentially serves to remove ammonia and further undesired by-products which can be removed with steam from the reaction mixture. The steam treatment preferably takes place at least between the main polymerization and after-polymerization. The pH of the polymerization product is preferably adjusted to a value of at most 6 prior to the steam treatment. The temperature of the steam used and of the polymer solution treated is preferably at least 90° C.

Copolymers A) which contain base groups can be partially or completely neutralized. Polymers with amine groups can also be converted into cationic groups using quaternizing agents, e.g. with alkylating agents, such as $C_1$-$C_4$-alkyl halides or sulfates. Examples of such alkylating agents are ethyl chloride, ethyl bromide, methyl chloride, methyl bromide, dimethyl sulfate and diethyl sulfate. The resulting salts of the polymers generally have a better solubility in water or dispersibility in water than the non-neutralized or quaternized polymers.

If an organic solvent is used in the preparation of the polymers, then this can be removed by customary methods known to the person skilled in the art, e.g. by distillation at reduced pressure.

The polymer solutions can be converted into powder form by various drying processes, such as, for example, spray drying, fluidized spray drying, drum drying or freeze drying. Preference is given to using spray drying. The resulting dry polymer powders can advantageously again be converted into an aqueous solution or dispersion by dissolution or redispersion, respectively, in water. Pulverulent copolymers have the advantage of better storability, simpler transportation and generally exhibit a lower tendency for microbial attack.

The invention also provides the copolymers A).

The cosmetically acceptable carrier B) is preferably chosen from
i) water,
ii) water-miscible organic solvents, preferably $C_1$-$C_4$-alkanols,
iii) oils, fats, waxes,
iv) esters different from iii) of $C_6$-$C_{30}$-monocarboxylic acids with mono-, di- or trihydric alcohols,
v) saturated acylic and cyclic hydrocarbons,
vi) fatty acids,
vii) fatty alcohols
and mixtures thereof.

The compositions according to the invention have, for example, an oil or fat component B) which is chosen from: hydrocarbons of low polarity, such as mineral oils; linear saturated hydrocarbons, preferably with more than 8 carbon atoms, such as tetradecane, hexadecane, octadecane, etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalkohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are e.g. linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are available commercially for example under the name cyclomethicone.

Preferred oil or fat components B) are chosen from paraffin and paraffin oils; vaseline; natural fats and oils, such as castor oil, soybean oil, groundnut oil, olive oil, sunflower oil, sesame oil, avacado oil, cocoa butter, almond oil, peach kernel oil, ricinus oil, cod-liver oil, lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candelilla wax, spermaceti and mixtures of the abovementioned oil or fat components.

Suitable cosmetically and pharmaceutically compatible oil and fat components B) are described in Karl-Heinz Schrader, Grundlagen und Rezepturen der Kosmetika [Principles and Formulations of Cosmetics], 2nd edition, Verlag Huthig, Heidelberg, pp. 319-355, to which reference is hereby made.

Suitable hydrophilic carriers B) are chosen from water, 1-, 2- or polyhydric alcohols with preferably 1 to 8 carbon atoms, such as ethanol, n-propanol, isopropanol, propylene glycol, glycerol, sorbitol, etc.

The cosmetic compositions according to the invention may be skin cosmetic, dermatological or hair cosmetic compositions.

The compositions according to the invention are preferably used in the form of a gel, foam, spray, an ointment, cream, emulsion, suspension, lotion, milk or paste. If desired, liposomes or microspheres can also be used.

The cosmetically or pharmaceutically active compositions according to the invention can additionally comprise cosmetically and/or dermatologically active ingredients and auxiliaries.

Preferably, the cosmetic compositions according to the invention comprise at least one copolymer A defined as above, at least one carrier B defined as above, and at least one constituent different from copolymer A which is chosen from cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaching agents, gel formers, care agents, colorants, tinting agents, tanning agents, dyes, pigments, consistency-imparting agents, humectants, refatting agents, collagen, protein hydrolysates, lipids, antioxidants, antifoams, antistats, emollients, softeners. Suitable thickeners are, for example, the Aculyn® grades from Rohm and Haas, such as Aculyn® 22 (copolymer of acrylates and methacrylic acid ethoxylates with stearyl radical (20 EO units)) and Aculyn® 28 (copolymer of acrylates and methacrylic acid ethoxylates with behenyl radical (25 EO units)).

Suitable cosmetically and/or dermatologically active ingredients are, for example, coloring active ingredients, skin and hair pigmentation agents, tinting agents, tanning agents, bleaches, keratin-hardening substances, antimicrobial active ingredients, light filter active ingredients, repellent active ingredients, substances with hyperemic activity, substances with keratolytic and keratoplastic activity, antidandruff active ingredients, antiphlogistics, substances which have a keratinizing action, substances with act as antioxidants or as free-radical scavengers, skin moisturizers or humectants, refatting active ingredients, antierythematous or antiallergic active ingredients and mixtures thereof.

Active ingredients which tan the skin artificially and which are suitable for tanning the skin without natural or artificial irradiation with UV rays are, for example, dihydroxyacetone, alloxan and walnut shell extract. Suitable keratin-hardening substances are usually active ingredients as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus serve both as preservatives and also as a deodorizing substance which prevents the formation or the intensity of body odor. These include, for example, customary preservatives known to the person skilled in the art, such as p-hydroxybenzoates, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable light filter active ingredients are substances which absorb UV rays in the UV-B- and/or UV-A region. Suitable UV filters are, for example, 2,4,6-triaryl-1,3,5-triazines in which the aryl groups may each carry at least one substituent which is preferably chosen from hydroxyl, alkoxy, specifically methoxy, alkoxycarbonyl, specifically methoxycarbonyl and ethoxycarbonyl and mixtures thereof. Also suitable are p-aminobenzoates, cinnamates, benzophenones, camphor derivatives, and pigments which stop UV rays, such as titanium dioxide, talc and zinc oxide. Suitable repellent active ingredients are compounds which are able to drive away or keep away certain animals, in particular insects, from humans. These include, for example, 2-ethyl-1,3-hexanediol, N,N-diethyl-m-toluamide etc. Suitable substances with hyperemic activity, which stimulate blood flow through the skin are, for example, ethereal oils, such as dwarf pine, lavender, rosemary, juniper berry, horsechestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, potassium thioglycolate, thioglycolic acid and salts thereof, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counter skin irritations, are, for example, allantoin, bisabolol, Dragosantol, camomile extract, panthenol, etc.

The cosmetic compositions according to the invention can comprise, as cosmetic and/or pharmaceutical active ingredient (and also optionally as auxiliary), at least one cosmetically or pharmaceutically acceptable polymer different from compounds of component A). Very generally, these include anionic, cationic, amphoteric and neutral polymers.

Examples of anionic polymers are homopolymers and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luviflex® Soft and Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxyfunctional, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are available commercially, for example, under the names Resyn® (National Starch) and Gafset® (GAF), and vinylpyrrolidone/vinyl acrylate copolymers, obtainable, for example, under the trade name Luviflex® (BASF). Other suitable polymers are the vinylpyrrolidone/acrylate terpolymer available under the name Luviflex® VBM-35 (BASF), and sodium sulfonate-containing polyamides or sodium sulfonate-containing polyesters.

Further suitable polymers are cationic polymers with the INCI name Polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamidocopolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), Polymer JR (hydroxyethylcellulose with cationic groups) and vegetable-based cationic polymers, e.g. guar polymers, such as the Jaguar® grades from Rhodia.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, e.g. those based on itaconic acid and aliphatic diamines, as are described, for example, in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and zwitterionic polymers as are disclosed, for example, in the German patent applications DE 39 29 973, DE 21 50 557, DE 28 17 369 and DE 37 08 451. Arylamidopropyltrimethylammonium chloride/acrylic acid or methacrylic acid copolymers and the alkali metal and ammonium salts thereof are preferred zwitterionic polymers. Other suitable zwitterionic polymers are methacroylethylbetaine/methacrylate copolymers, which are available commercially under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyether siloxanes, such as Tegopren® (Goldschmidt) or Belsil® (Wacker).

The formulation base of pharmaceutical compositions according to the invention preferably comprises pharmaceutically acceptable auxiliaries. Pharmaceutically acceptable auxiliaries are the auxiliaries which are known for use in the fields of pharmacy, food technology and related fields, in particular the auxiliaries listed in the relevant pharmacopeias (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, anti-irritative substances, chelating agents, emulsion stabilizers, film formers, gel formers, odor-masking agents, resins, hydrocolloids, solvents, solubility promoters, neutralizing agents, permeation accelerators, pigments, quaternary ammonium compounds, refatting and superfatting agents, ointment bases, cream bases or oil bases, silicone derivatives, stabilizers, sterilizing agents, propellants, drying agents, opacifiers, thickeners, waxes, softeners, white oils. Formulation in this regard is based on expert knowledge, as given, for example, in Fiedler, H. P. Lexikon der Hilfsstoffe für Pharmazie, Kosmetik und angrenzende Gebiete [Lexicon of auxiliaries for pharmacy, cosmetics and related fields], 4th edn., Aulendorf: ECV-Editio-Kantor-Verlag, 1996.

To prepare the dermatological compositions according to the invention, the active ingredients can be mixed or diluted with a suitable auxiliary (excipient). Excipients can be solid, semisolid or liquid materials which can also serve as vehicles, carriers or medium for the active ingredient. The admixing of further auxiliaries is carried out, where desired, in the manner known to the person skilled in the art.

In a first preferred embodiment, the compositions according to the invention are skin-cleansing compositions.

Preferred skin-cleansing compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations.

According to a further preferred embodiment, the compositions according to the invention are cosmetic compositions for the care and protection of the skin, nailcare compositions or preparations for decorative cosmetics.

Particular preference is given to skincare compositions, personal hygiene compositions, footcare compositions, light protection compositions, repellents, shaving compositions, depilatory compositions, antiacne compositions, make-up, mascara, lipsticks, eye shadows, kohl pencils, eyeliners, blushers and eyebrow pencils.

The skincare compositions according to the invention are, in particular, W/O or O/W skin creams, day creams and night creams, eye creams, face creams, antiwrinkle creams, moisturizing creams, bleaching creams, vitamin creams, skin lotions, care lotions and moisturizing lotions.

Skin cosmetic and dermatological compositions based on the above-described polymers A) exhibit advantageous effects. The polymers can, inter alia, contribute to the moisturizing and conditioning of the skin and to an improvement in the feel of the skin. The polymers can also act as thickeners in the formulations. By adding the polymers according to the invention, it is possible to achieve a considerable improvement in skin compatibility in certain formulations.

Skin cosmetic and dermatological compositions preferably comprise at least one copolymer A) in an amount of from about 0.001 to 30% by weight, preferably 0.01 to 20% by weight, very particularly preferably 0.1 to 12% by weight, based on the total weight of the composition.

Light protection agents based on the copolymers A), in particular, have the property of increasing the residence time of the UV-absorbing ingredients compared with customary auxiliaries such as polyvinylpyrrolidone.

Depending on the field of use, the compositions according to the invention can be applied in a form suitable for skin care, such as, for example, as cream, foam, gel, pencil, mousse, milk, spray (pump spray or spray containing propellant) or lotion.

As well as comprising the polymers A) and suitable carriers, the skin cosmetic preparations can also comprise further active ingredients and auxiliaries customary in skin cosmetics and as described above. These include, preferably, emulsifiers, preservatives, perfume oils, cosmetic active ingredients, such as phytantriol, vitamins A, E and C, retinol, bisabolol, panthenol, light protection agents, bleaches, colorants, tinting agents, tanning agents, collagen, protein hydrolyzates, stabilizers, pH regulators, dyes, salts, thickeners, gel formers, bodying agents, silicones, moisturizers, refatting agents and further customary additives.

Preferred oil and fatty components of the skin cosmetic and dermatological compositions are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The polymers according to the invention can also be mixed with traditional polymers where specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are prepared by customary processes known to the person skilled in the art.

The cosmetic and dermatological compositions are preferably in the form of emulsions, in particular as water-in-oil (W/O) emulsions or oil-in-water (O/W) emulsions. It is, however, also possible to choose other types of formulation, for example hydrodispersions, gels, oils, oleogels, multiple emulsions, for example in the form of W/O/W or O/W/O emulsions, anhydrous ointments or ointment bases, etc.

The emulsions are prepared by known methods. Apart from the copolymer A), the emulsions usually comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The choice of emulsion type-specific additives and the preparation of suitable emulsions is described, for example, in Schrader, Grundlagen und Rezepturen der Kosmetika [Principles and Formulations of Cosmetics], Huthig Buch Verlag, Heidelberg, 2nd edition, 1989, third part, to which express reference is made here.

A suitable emulsion, e.g. for a skin cream etc., generally comprises an aqueous phase which is emulsified by means of a suitable emulsifier system in an oil or fatty phase.

The proportion of the emulsifier systems in this type of emulsion is preferably about 4 to 35% by weight, based on the total weight of the emulsion. The proportion of the fatty phase is preferably about 20 to 60% by weight. The proportion of the aqueous phase is preferably about 20 to 70%, in each case based on the total weight of the emulsion. The emulsifiers are those customarily used in this type of emulsion. They are chosen, for example, from: $C_{12}$-$C_{18}$-sorbitan fatty acid esters; esters of hydroxystearic acid and $C_{12}$-$C_{30}$-fatty alcohols; mono- and diesters of $C_{12}$-$C_{18}$-fatty acids and glycerol or polyglycerol; condensates of ethylene oxide and propylene glycols; oxypropylenated/oxyethylated $C_{12}$-$C_{18}$-fatty alcohols; polycyclic alcohols, such as sterols; aliphatic alcohols with a high molecular weight, such as lanolin; mixtures of oxypropylenated/polyglycerolated alcohols and magnesium isostearate; succinic esters of polyoxyethylenated or polyoxypropylenated fatty alcohols; and mixtures of magnesium lanolate, calcium lanolate, lithium lanolate, zinc lanolate or aluminum lanolate and hydrogenated lanolin or lanolin alcohol.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is at about 250° C. and whose distillation end-point is at 410° C., such as, for example, vaseline oil; esters of saturated or unsaturated fatty acids, such as alkyl myristates, e.g. i-propyl, butyl or cetyl myristate, hexadecyl stearate, ethyl or i-propyl palmitate, octanoic or decanoic acid triglycerides and cetyl ricinoleate.

The fatty phase may also comprise silicone oils soluble in other oils, such as dimethylpolysiloxane, methylphenylpolysiloxane and the silicone glycol copolymer, fatty acids and fatty alcohols.

In order to favor the retention of oils, in addition to the polymers A), it is also possible to use waxes, such as, for example, carnauba wax, candelilla wax, beeswax, microcrystalline wax, ozokerite wax and the oleates, myristates, linoleates and stearates of Ca, Mg and Al.

The water-in-oil emulsions are generally prepared by introducing the fatty phase and the emulsifier into a reaction vessel. The vessel is heated at a temperature of approximately 50 to 75° C., then the active ingredients and/or auxiliaries which are soluble in oil are added, and water which has been heated beforehand to approximately the same temperature and into which the water-soluble ingredients have optionally been dissolved beforehand is added with stirring. The mixture is stirred until an emulsion of the desired fineness is achieved, which is then left to cool to room temperature, if necessary with a lesser amount of stirring.

According to a further preferred embodiment, the compositions according to the invention are a shower gel, a shampoo formulation or a bath preparation.

Such formulations comprise at least one polymer A) and customarily anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickeners/gel formers, skin conditioning agents and humectants.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants customarily used in body-cleansing compositions can be used in washing, shower and bath preparations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The washing, shower and bath preparations can also comprise customary cationic surfactants such as, for example, quaternary ammonium compounds, for example cetyltrimethylammonium chloride.

In addition, it is also possible to use other customary cationic polymers, such as, for example, copolymers of acrylamide and dimethyldiallylammonium chloride (Polyquaternium-7), cationic cellulose derivatives (Polyquaternium-4, -10), guar hydroxypropyltrimethylammonium chloride (INCI: Hydroxylpropyl Guar Hydroxypropyltrimonium Chloride), copolymers of N-vinylpyrrolidone and quaternized N-vinylimidazole (Polyquaternium-16, -44, -46), copolymers of N-vinylpyrrolidone/dimethylaminoethyl methacrylate, quaternized with diethyl sulfate (Polyquaternium-11) and others.

The shower gel/shampoo formulations can further comprise thickeners, such as, for example sodium chloride, PEG-55, propylene glycol oleate, PEG-120, methyl glucose dioleate and others, and also preservatives, further active ingredients and auxiliaries and water.

In a further preferred embodiment the compositions according to the invention are hair-treatment compositions.

Hair-treatment compositions according to the invention preferably comprise at least one copolymer A) in an amount in the range from about 0.1 to 30% by weight, preferably 0.5 to 20% by weight, based on the total weight of the composition.

The hair-treatment compositions according to the invention are preferably in the form of a setting foam, hair mousse, hair gel, shampoo, hairspray or hair foam. Hairsprays include both aerosol sprays and also pump sprays without propellant gas. Hair foams include both aerosol foams and also pump foams without propellant gas.

Preferred hair-treatment compositions are in the form of a gel. Such a hair-treatment composition comprises, for example:
a) 0.1 to 20% by weight, preferably 1 to 10% by weight, of at least polymer A), as defined above,
b) 0 to 40% by weight of at least one carrier (solvent) which is chosen from $C_2$-$C_5$-alcohols, in particular ethanol,
c) 0.01 to 5% by weight, preferably 0.2 to 3% by weight, of at least one thickener,
d) 0 to 50% by weight of a propellent,
e) 0 to 10% by weight, preferably 0.1 to 3% by weight, of at least one setting polymer different from a), preferably a water-soluble nonionic polymer,
f) 0 to 1% by weight of at least one refatting agent, preferably chosen from glycerol and glycerol derivatives,
g) 0 to 30% by weight of further active ingredients and/or auxiliaries, e.g. at least one silicone compound,
h) water ad 100% by weight.

The hair-treatment compositions can also be in the form of hairsprays or hair foams. Hairsprays and hair foams preferably comprise predominantly or exclusively water-soluble or water-dispersible components. If the compounds used in the hairsprays and hair foams according to the invention are water-dispersible, they can be used in the form of aqueous microdispersions with particle diameters of, usually, 1 to 350 nm, preferably 1 to 250 nm. The solids contents of these preparations are customarily in a range from about 0.5 to 20% by weight. These microdispersions generally do not require emulsifiers or surfactants for their stabilization.

Preferred hair-treatment compositions are in the form of an aqueous dispersion or in the form of an alcoholic or aqueous-alcoholic solution. Examples of suitable alcohols are ethanol, propanol, isopropanol and mixtures thereof.

Furthermore, the hair-treatment compositions according to the invention can generally comprise customary cosmetic auxiliaries, for example softeners, such as glycerol and glycol; emollients; perfumes; surfactants; UV absorbers; dyes; antistatic agents; agents for improving combability; preservatives; and antifoams.

If the compositions according to the invention are formulated as hairspray, they comprise a sufficient amount of a propellant, for example a low-boiling hydrocarbon or ether, such as propane, butane, isobutane or dimethyl ether. Propellants which can also be used are compressed gases, such as nitrogen, air or carbon dioxide. The amount of propellant here can be kept low in order not to increase the VOC content unnecessarily. This is then generally not more than 55% by weight, based on the total weight of the composition. If desired, however, higher VOC contents of 85% by weight and above are also possible.

The above-described polymers A) can also be used in combination with other hair polymers in the compositions. Suitable polymers are those described above.

The other hair polymers are preferably present in amounts up to 10% by weight, based on the total weight of the composition.

A preferred hair-treatment composition in the form of a hairspray or hair foam comprises:
a) 0.5 to 20% by weight, preferably 1 to 10% by weight, of at least one polymer A), as defined above,
b) 50 to 99.5% by weight, preferably 55 to 99% by weight, of a carrier (solvent), chosen from water and water-miscible solvents, preferably $C_2$-$C_5$-alcohols, in particular ethanol, and mixtures thereof,
c) 0 to 70% by weight, preferably 0.1 to 50% by weight, of a propellant, preferably chosen from dimethyl ether and alkanes, such as, for example, propane/butane mixtures,
d) 0 to 10% by weight, preferably 0.1 to 10% by weight, of at least one hair polymer different from a), preferably a water-soluble or -dispersible polymer,
e) 0 to 0.5% by weight, preferably 0.001 to 2% by weight, of at least one water-soluble or water-dispersible silicone compound,
and optionally further active ingredients and/or auxiliaries, as defined above.

The composition according to the invention can comprise, as component e), at least one nonionic, siloxane-containing, water-soluble or -dispersible polymer, in particular chosen from the above-described polyether siloxanes. The proportion of this component is then generally about 0.001 to 2% by weight, based on the total weight of the composition.

The copolymers A) are suitable in an advantageous way as auxiliaries in pharmacy, preferably as or in (a) coating(s) for the textile, paper, printing and leather industry.

The present invention further provides a process for the preparation of a copolymer A defined as above by free-radical polymerization of the monomers a) with at least one further monomer chosen from the monomers b) and c), optionally in the presence of up to 25% by weight, based on the total weight of components a) to d), of a water-soluble component d), wherein the polymerization is carried out in an aqueous solvent. The above statements regarding the preferred embodiments of the polymerization for the preparation of the copolymer A according to the invention are correspondingly valid here.

The invention is illustrated in more detail by reference to the nonlimiting examples below.

EXAMPLES

General preparation procedure for examples 1 to 50 and Comparative examples A to D: solution polymerization (example 10)

| | | |
|---|---|---|
| Feed 1: | Monomer mixture of: | |
| | 240 g | (50% strength aqueous solution) of acrylamide and |
| | 533.4 g | (15% strength aqueous solution) of methacrylamide |
| Feed 2: | Monomer mixture of: | |
| | 120 g | of vinylpyrrolidone and |
| | 80 g | of vinylcaprolactam |
| Feed 3: | Initiator solution of: | |
| | 4 g | of Wako V 50 [2,2'-azobis (2-amidinopropane) dihydrochloride] and |
| | 180 g | of water |
| Feed 4: | Initiator solution of: | |
| | 2 g | of Wako V 50 [2,2'-azobis (2-amidinopropane) dihydrochloride] and |
| | 90 g | of water |
| Feed 5: | 1 g | of 90% by weight lactic acid in 9 g of water |

10% of feed 1, 20% of feed 2 and 10% of feed 3 in 490 g of water were introduced into a stirred apparatus with reflux condenser, internal thermometer and four separate feed devices, and the mixture was heated to about 60° C. with stirring. Following the onset of polymerization, recognizable from the viscosity starting to increase, at 65° C., the remainder of feed 1 was added over the course of three hours, the remainder of feed 2 was added over the course of 1.5 hours and the remainder of feed 3 was added over the course of four hours. In an alternative embodiment, the pH of the reaction solution was adjusted to 6.4 to 7.4 using feed 5. When the addition was complete, the mixture was afterpolymerized for a further two hours at this temperature. Then, for the afterpolymerization, feed 4 was added over the course of 30 minutes at 65° C. and, when the addition was complete, the mixture was afterpolymerized for about a further two hours at this temperature and for a further two hours at a temperature of from 80 to 90° C. In an alternative embodiment, the reaction mixture was then treated for a further 1 h with steam at a pH of about 6. This gave an approximately 30% aqueous microdispersion. For stabilization, the solution is treated with 100 ppm of Euxyl®K 100 from Schulke & Mayr (5-chloro-2-methyl-3-(2H)-isothiazolone/2-methyl-3-(2H)-isothiazolone/benzyl alcohol). If water/ethanol mixtures are used, it is not necessary to use a stabilizer.

Pulverulent products can be obtained by spray-drying or freeze-drying. All of the products in the list below were polymerized analogously.

TABLE 1

| Ex. No. | AM | MAM | VP | VCap | VFA | DMAA | 350-MA | Q-DMAEMA | C-Dry MD1934 | PVOH |
|---|---|---|---|---|---|---|---|---|---|---|
| A | — | — | — | — | — | — | — | — | — | — |
| B | 100 | — | — | — | — | — | — | — | — | — |
| C | — | — | — | — | 100 | — | — | — | — | — |
| D | — | — | 100 | — | — | — | — | — | — | — |
| 1 | 80 | — | 20 | — | — | — | — | — | — | — |
| 2 | 80 | — | — | — | — | 20 | — | — | — | — |
| 3 | 50 | 30 | — | — | — | — | 20 | — | — | — |
| 4 | 70 | — | 30 | — | — | — | — | — | — | — |
| 5 | 70 | — | — | — | — | 30 | — | — | — | — |
| 6 | 60 | — | 40 | — | — | — | — | — | — | — |
| 7 | 60 | — | — | — | — | 40 | — | — | — | — |
| 8 | 30 | 30 | 40 | — | — | — | — | — | — | — |
| 9 | 50 | — | 50 | — | — | — | — | — | — | — |
| 10 | 30 | 20 | 30 | 20 | — | — | — | — | — | — |
| 11 | 40 | — | 60 | — | — | — | — | — | — | — |
| 12 | 40 | — | 30 | 30 | — | — | — | — | — | — |
| 13 | 40 | — | 20 | — | 30 | — | — | — | — | 5 |
| 14 | 20 | 20 | 40 | — | — | 20 | — | — | — | — |
| 15 | — | 40 | 60 | — | — | — | — | — | — | — |
| 16 | — | 40 | 55 | — | — | — | — | — | — | 5 |
| 17 | — | 40 | 50 | 10 | — | — | — | — | — | — |
| 18 | — | 40 | 30 | 30 | — | — | — | — | — | — |
| 19 | — | 40 | 30 | — | 20 | — | — | — | — | 10 |
| 20 | — | 35 | 35 | — | 15 | — | 5 | — | — | 5 |
| 21 | 30 | — | 70 | — | — | — | — | — | — | — |
| 22 | 30 | — | 65 | — | — | 5 | — | — | — | — |
| 23 | 30 | — | 60 | — | — | 10 | — | — | — | — |
| 24 | 30 | — | 40 | 30 | — | — | — | — | — | — |
| 25 | — | 30 | 70 | — | — | — | — | — | — | — |
| 26 | — | 30 | 30 | — | 30 | — | — | — | — | 10 |
| 27 | 25 | — | 55 | 20 | — | — | — | — | — | — |
| 28 | — | 25 | 40 | — | 30 | — | — | — | — | 5 |
| 29 | 20 | — | 60 | 20 | — | — | — | — | — | — |
| 30 | 20 | — | 40 | 20 | — | 20 | — | — | — | — |
| 31 | — | 20 | 40 | — | 35 | — | — | — | — | 5 |
| 32 | — | 20 | — | 30 | 35 | — | 5 | — | — | 10 |
| 33 | 95 | — | — | — | — | — | — | 5 | — | — |
| 34 | 50 | 15 | — | — | 20 | — | 5 | — | — | 10 |
| 35 | 30 | 30 | — | — | 20 | — | — | 10 | — | 10 |
| 36 | 40 | — | 58 | — | — | — | 2 | — | — | — |
| 37 | — | 30 | 35 | — | 20 | — | 5 | — | — | 10 |
| 38 | — | 30 | — | — | 50 | — | 5 | 5 | — | 10 |
| 39 | 80 | — | — | — | — | — | — | — | 20 | — |
| 40 | 30 | 30 | — | — | 20 | — | — | — | 20 | — |
| 41 | 50 | — | 30 | — | — | — | — | — | 20 | — |
| 42 | 40 | — | 25 | — | 25 | — | — | — | 10 | — |
| 43 | — | 30 | 60 | — | — | — | — | — | 10 | — |
| 44 | — | 30 | 30 | — | 30 | — | — | — | 10 | — |
| 45 | — | 30 | 30 | — | 30 | — | 5 | — | 5 | — |
| 46 | — | 30 | 30 | — | 30 | — | — | 3 | 7 | — |

TABLE 1-continued

| Ex. No. | AM | MAM | VP | VCap | VFA | DMAA | 350-MA | Q-DMAEMA | C-Dry MD1934 | PVOH |
|---|---|---|---|---|---|---|---|---|---|---|
| 47 | — | 25 | 70 | — | — | — | — | — | 5 | — |
| 48 | — | 25 | 35 | — | 30 | — | — | 2 | 8 | — |
| 49 | — | 20 | 70 | — | — | — | — | — | 10 | — |
| 50 | — | 20 | 40 | — | 30 | — | — | — | 10 | — |

| | |
|---|---|
| AM | acrylamide |
| MAM | methacrylamide |
| VP | N-vinylpyrrolidone |
| VCap | N-vinylcaprolactam |
| VFA | N-vinylformamide |
| DMAA | dimethylacrylamide |
| 350-MA | polyethylene glycol methacrylate (Mn = 350) |
| Q-DMAEMA | dimethylaminoethyl methacrylate-dimethyl sulfate |
| C-Dry MD1934 | degraded starch (dextrose equivalent DE = 38; Cerestar) |
| PVOH | partially saponified polyvinyl alcohol (Mowiol ® 4-88, Clariant) |

General preparation procedure for examples 51 to 65: solution polymerization with after-polymerization and steam treatment (example 63)

| | | |
|---|---|---|
| Feed 1: | Monomer mixture of: | |
| | 120 g | of vinylpyrrolidone and |
| | 2 g | of vinylimidazole |
| Feed 2: | 466.7 g | of a 15% strength aqueous solution of methacryl (=70 g of methacrylamide) |
| Feed 3: | Initiator solution of: | |
| | 2 g | of Wako V 50 [2,2'-azobis(2-amidinopropane) dihydrochloride] and |
| | 18 g | of water |
| Feed 4: | Initiator solution of: | |
| | 2 g | of Wako V 50 [2,2'-azobis(2-amidinopropane) dihydrochloride] and |
| | 90 g | of water |
| Feed 5: | 3 g | of 25% strength lactic acid solution |
| Initial charge: | 26.7 g | of a 50% strength aqueous polyvinyl alcohol solution (=8 g of Mowiol ® 4-88) |

30.5 g of feed 1, 117 g of feed 2 and 4 g of feed 3 in 150 g of water were initially introduced into a stirred apparatus with reflux condenser, internal thermometer and four separate feed devices, and the mixture was heated to about 65° C. with stirring. Following the onset of polymerization, recognizable from the viscosity starting to increase, at 65° C., the remainder of feed 1 was added over the course of 3 hours, the remainder of feed 2 was added over the course of 5 hours and the remainder of feed 3 was added over the course of 6 hours, the internal temperature being increased to about 67° C. When the addition was complete, the reaction mixture was left at this temperature for about a further 2 hours. The polymer solution was treated with steam for 30 minutes. Feed 4 was then added over the course of 30 minutes and feed 5 was added over the course of 5 minutes, and the polymer solution was after-polymerized for about a further 3 hours at a temperature of about 70° C. This gave about 800 g of an about 22% strength polymer solution. The solution was treated wtih steam for about 1 hour and stirred at a temperature of about 100° C. for a further 2 hours.

For stabilization, the solution was treated with 100 ppm of Euxyl K100 from Schülke & Mayr (5-chloro-2-methyl-3-(2)-isothiazolone/2-methyl-3-(2H)-isothiazolone/benzyl alcohol).

Pulverulent products were obtained by spray-drying or freeze-drying.

All of the products listed in table 2 below were polymerized analogously.

TABLE 2

| Ex. No. | MAM | VP | VCap | DMAA | 350-MA | VI | PVOH |
|---|---|---|---|---|---|---|---|
| 51 | 5 | 70 | 25 | — | — | — | — |
| 52 | 10 | 70 | 10 | — | 10 | — | — |
| 53 | 10 | 70 | 15 | — | — | 5 | — |
| 54 | 10 | 67 | 20 | — | — | 3 | — |
| 55 | 20 | 70 | — | 10 | — | — | — |
| 56 | 20 | 70 | — | — | 5 | 5 | — |
| 57 | 20 | 68 | 10 | — | — | 2 | — |
| 58 | 20 | 70 | — | — | — | 4 | 6 |
| 59 | 20 | 72 | — | — | — | 3 | 5 |
| 60 | 25 | 62 | 10 | — | — | 3 | — |
| 61 | 25 | 72 | — | — | — | 3 | — |
| 62 | 30 | 68 | — | — | — | 2 | — |
| 63 | 35 | 60 | — | — | — | 1 | 4 |
| 64 | 38 | 60 | — | — | — | 2 | — |
| 65 | 40 | 58 | — | — | — | 2 | — |

| | |
|---|---|
| VI: | vinylimidazole |
| VCap: | N-vinylcaprolactam |
| DMAA: | dimethylacrylamide |
| 350-MA: | polyethylene glycol methacrylate ($M_n$ 350) |
| PVOH: | partially saponified polyvinyl alcohol (Mowiol ® 4-88, Clariant) |

Performance Properties

Standard Formulation:

0.5% by weight of a standard commercial polyacrylic acid thickener (Carbopol 940, BFGoodrich), neutralized with triethanolamine (TEA), is used to formulate a gel which, when applied to the hair, exhibits essentially no conditioning or setting action. The performance properties are shown in table 3, comparative example A.

Comparative Examples B-D

3% by weight of a standard commercial hair polymer (Ex. B: polyacrylamide, C: polyvinylformamide, D: polyvinylpyrrolidone) were added in each case to the gel formulation from the standard formulation. The performance properties are shown in table 2. The products are still in need of improvement with regard to their tackiness.

In Accordance with the Invention:

3% by weight of the copolymers 1 to 67 are in each case added as hair cosmetic active ingredient to the gel formulation from the standard formulation. This gives clear formulations with good conditioning or setting action. The application properties are likewise given in table 3.

Evaluation:

A) Clarity

| Grade | Clarity | |
|---|---|---|
| 1 | clear | (reference: Carbopol 940; polyvinylformamide with K value = 40) |
| 1-2 | almost clear | (reference: Luviskol ® VA 64) |
| 2 | hand clear | (clear with the formation of a thin film on the hand; reference: polyvinylformamide with K value = 110; Luviskol ® VA 73) |
| 3 | slightly cloudy | (reference: polyvinylpyrrolidone K 90) |
| 4 | cloudy | (reference: polyvinyl alcohol, e.g. Mowiol ® 4-88) |
| 5 | milky | |

B) Viscosity

| Grade | Viscosity |
|---|---|
| 1 | very solid (reference: gel of 0.5% Carbopol 940/TEA) |
| 2 | solid |
| 3 | moderately solid |
| 4 | flowable |
| 5 | low-viscosity |

C) Tackiness

The tackiness was determined at a relative atmospheric humidity of 75% and an ambient temperature directly on dried films of the gel formulations.

| Grade | Tackiness |
|---|---|
| 1 | not tacky |
| 2 | slightly tacky |
| 3 | moderately tacky |
| 4 | tacky |
| 5 | very tacky |

TABLE 3

| Ex. No. | A grade (clarity of the gel) | B grade (viscosity of the gel) | C grade (tackiness of the dried gel film) |
|---|---|---|---|
| A | Gel of 0.5% Carbopol 940/TEA | | |
| | 1 | 1-2 | 1 (hard, brittle, incomplete film) |
| B | Gel of 3% polymer + 0.5% Carbopol 940/TEA | | |
| | 3-4 | 2 | 1-2 |
| C | Gel of 3% polymer + 0.5% Carbopol 940/TEA | | |
| | 1 | 1-2 | 2-3 |
| D | Gel of 3% polymer + 0.5% Carbopol 940/TEA | | |
| | 1 | 1-2 | 3 |
| 1 | 2 | 1-2 | 2 |
| 2 | 1-2 | 1 | 1-2 |
| 3 | 1-2 | 1-2 | 2 |
| 4 | 1-2 | 1-2 | 2 |
| 5 | 1-2 | 1-2 | 1-2 |
| 6 | 1-2 | 1-2 | 2 |
| 7 | 1-2 | 1-2 | 1-2 |
| 8 | 1-2 | 1-2 | 1-2 |
| 9 | 1 | 1-2 | 1-2 |
| 10 | 2 | 1-2 | 1-2 |
| 11 | 1 | 1-2 | 1-2 |
| 12 | 2 | 1 | 1 |
| 13 | 1 | 1 | 1-2 |
| 14 | 2 | 2 | 2 |
| 15 | 1 | 1-2 | 1-2 |
| 16 | 1 | 1 | 1 |
| 17 | 1 | 1 | 1 |
| 18 | 2 | 1 | 1-2 |
| 19 | 1-2 | 1 | 1-2 |
| 20 | 1-2 | 1 | 1-2 |
| 21 | 1 | 1-2 | 2 |
| 22 | 1 | 1-2 | 2 |
| 23 | 1-2 | 1-2 | 2 |
| 24 | 1-2 | 1 | 1-2 |
| 25 | 1-2 | 1-2 | 1-2 |
| 26 | 1 | 1-2 | 1-2 |
| 27 | 1-2 | 1-2 | 1-2 |
| 28 | 1 | 1-2 | 1-2 |
| 29 | 1-2 | 1-2 | 1-2 |
| 30 | 1-2 | 1-2 | 2 |
| 31 | 1 | 1 | 1-2 |
| 32 | 1-2 | 1-2 | 1-2 |
| 33 | 1-2 | 1-2 | 2 |
| 34 | 1-2 | 2 | 1-2 |
| 35 | 1-2 | 2 | 2 |
| 36 | 1-2 | 1-2 | 1-2 |
| 37 | 1-2 | 1-2 | 1-2 |
| 38 | 1-2 | 1-2 | 2 |
| 39 | 1-2 | 1 | 2 |
| 40 | 1 | 1 | 2 |
| 41 | 1-2 | 1 | 2 |
| 42 | 1 | 1-2 | 1-2 |
| 43 | 1-2 | 1-2 | 1-2 |
| 44 | 1-2 | 1 | 1 |
| 45 | 1 | 1 | 1-2 |
| 46 | 1 | 1 | 1-2 |
| 47 | 1-2 | 1-2 | 1-2 |
| 48 | 1 | 1-2 | 1-2 |
| 49 | 1 | 1-2 | 1-2 |
| 50 | 1 | 1 | 1-2 |
| 51 | 1-2 | 1 | 1 |
| 52 | 1 | 1 | 1-2 |
| 53 | 1 | 1 | 1-2 |
| 54 | 1 | 1 | 1 |
| 55 | 1 | 1 | 1-2 |
| 56 | 1 | 1 | 1-2 |
| 57 | 1 | 1 | 1 |
| 58 | 1 | 1 | 1 |
| 59 | 1 | 1 | 1 |
| 60 | 1-2 | 1 | 1 |
| 61 | 1 | 1 | 1 |
| 62 | 1 | 1 | 1 |
| 63 | 1 | 1 | 1 |
| 64 | 1 | 1 | 1 |
| 65 | 1 | 1 | 1 |

The clarity of the gels can be improved further by the addition of up to 20% by weight of ethanol.

Use in Hair Cosmetics:

1) Hair Gels Containing an Anionic Thickener: Examples No. 1-50

| | [%] | CTFA |
|---|---|---|
| Phase 1: | | |
| Polymer 1-50 (30% strength aqueous solution) | 10.0 | |
| Glycerol | 0.3 | |
| Water dist. | 39.2 | |
| Further additives: preservative, soluble ethoxylated silicone, perfume | q.s. | |

-continued

| | [%] | CTFA |
|---|---|---|
| Phase 2: | | |
| Carbopol 940 (1% strength aqueous suspension) | 30.0 | Carbomer |
| Triethanolamine | 0.5 | |
| Water dist. | 20.0 | |

To prepare the hair gel, the components are weighed in and homogenized. Here, phase 2 forms a clear, solid gel into which phase 1 is slowly stirred.

2) Hair Gels Containing a Further Setting Polymer and Anionic Thickener: Examples No. 51-100

| | [%] | CTFA |
|---|---|---|
| Phase 1: | | |
| Polymer 1-50 (30% strength aqueous solution) | 7.0 | |
| Luviskol VA 64 | 1.0 | vinylpyrrolidone-vinylacetate copolymer |
| Uvinul MS 40 | 0.2 | benzophenone-4 |
| Glycerol | 0.2 | |
| D-Panthenol USP | 0.1 | panthenol |
| Ethanol | 20.0 | |
| Water dist. | 21.0 | |
| Further additives: preservative, soluble ethoxylated silicone, perfume | q.s. | |
| Phase 2: | | |
| Carbopol 940 (1% strength aqueous suspension) | 30.0 | Carbomer |
| Triethanolamine | 0.5 | |
| Water dist. | 20.0 | |

Preparation: weigh in, and homogenize. Phase 2 forms a clear, solid gel. Slowly stir phase 1 into phase 2.

3) Liquid Hair Gels: Examples No. 101-138

| | [%] | CTFA |
|---|---|---|
| Polymer 1-38 (30% strength aqueous solution) | 5.0 | |
| Glycerol | 0.3 | |
| Natrosol 250 L (2% strength aqueous solution) | 25.0 | hydroxyethylcellulose (Hercules) |
| C-Dry MD 1915 (10% strength aqueous solution) | 25.0 | degraded starch (Cerestar) |
| Water dist. | 44.7 | |
| Further additives: preservative, soluble ethoxylated silicone, perfume | q.s. | |

Preparation: weigh in and slowly homogenize at room temperature

4) Aqueous Hand Pump Sprays: Examples No. 139-175

| | [%] | CTFA |
|---|---|---|
| Polymer 14-50 (30% strength aqueous solution) | 10.0 | |
| Luviset ® PUR (30% strength water/ethanol solution) | 5.0 | (PU disperion BASF) |
| C-Dry MD 1915 (10% strength aqueous solution) | 5.0 | degraded starch (Cerestar) |
| Water dist. | 45.0 | |
| Further additives: preservative, soluble ethoxylated silicone, perfume | q.s. | |

Preparation: weigh in and slowly homogenize at room temperature.

5) VOC 55 Hand Pump Spray: Examples No. 176-194

| | [%] | CTFA |
|---|---|---|
| Polymer 4-10, 11, 12, 15-18, 21-25, 27 (30% strength aqueous solution) | 10.0 | |
| Water dist. | 35.0 | |
| Ethanol | 55.0 | |
| Further additives: preservative, soluble ethoxylated silicone, perfume | q.s. | |

6) VOC 55 Aerosol Hairspray: Examples No. 195-213

| | [%] | CTFA |
|---|---|---|
| Polymer 4-10, 11, 12, 15-18, 21-25, 27 (30% strength aqueous solution) | 5.0 | |
| Luviset ® PUR (30% strength water/ethanol solution) | 5.0 | (PU dispersion BASF) |
| Water dist. | 35.5 | |
| Dimethyl ether | 30.0 | |
| Ethanol | 24.5 | |
| Further additives: preservative, soluble ethoxylated silicone, perfume | q.s. | |

7) Setting Foam: Examples No. 214-232

| | [%] | CTFA |
|---|---|---|
| Polymer 4-10, 11, 12, 15-18, 21-25, 27 (30% strength aqueous solution) | 5.0 | |
| Cremophor A 25 (Ceteareth 25/BASF) | 0.2 | |
| Comperlan KD (Coamide DEA/Henkel) | 0.1 | |
| Water dist. | 74.7 | |
| Dimethyl ether | 10.0 | |
| Further additives: preservative, soluble ethoxylated silicone, perfume | q.s. | |

Preparation: weigh in and dissolve with stirring. Bottle and add propellant gas.

8) Shampoo: Examples No. 233-272

| Conditioner Shampoo: | | |
|---|---|---|
| | [%] | CTFA |
| A) Texapon NSO 28% strength (sodium laurylsulfate/Henkel) | 50.0 | |
| Comperlan KD (Coamide DEA/Henkel) | 1.0 | |
| Polymer 1-38, 46, 48 (30% strength aqueous solution) | 3.0 | |
| Water dist. | 17.0 | |
| q.s. perfume oil | | |

33

-continued

| Conditioner Shampoo: | | |
|---|---|---|
| | [%] | CTFA |
| B) Water | 27.5 | |
| Sodium chloride | 1.5 | |
| q.s. preservative | | |

Preparation: weigh in and, with stirring, dissolve phases A) and B) separately and mix. Slowly stir phase B) into phase A).

Use in Skin Cosmetics:

9) Standard O/W Cream: Examples No. 273-290

| Oil phase: | [%] | CTFA |
|---|---|---|
| Cremophor A6 | 3.5 | ceteareth-6 and stearyl alcohol |
| Cremophor A25 | 3.5 | ceteareth-25 |
| Glycerol monostearate s.e. | 2.5 | glyceryl stearate |
| Paraffin oil | 7.5 | paraffin oil |
| Cetyl alcohol | 2.5 | cetyl alcohol |
| Luvitol EHO | 3.2 | cetearyl octanoate |
| Vitamin E acetate | 1.0 | tocopheryl acetate |
| Nip-Nip | 0.1 | methyl and propyl 4-hydroxy-benzoate (7:3) |

| Water phase: | [%] | |
|---|---|---|
| Polymer No. 3, 14, 16, 20-23, 30-38, 45, 46 (30% strength aqueous solution) | 3.0 | |
| Water | 74.6 | |
| 1,2-Propylene glycol | 1.5 | |
| Germall II | 0.1 | imidazolidinyl-urea |

Preparation: weigh in and, with stirring, homogenize the oil phase and the water phase separately at a temperature of 80° C. Slowly stir the water phase into the oil phase. Slowly cool to room temperature with stirring.

10) Day Lotion: Examples No. 291-308

| Oil phase: | [%] | CTFA |
|---|---|---|
| Cremophor A6 | 1.5 | ceteareth-6 and stearyl alcohol |
| Cremophor A25 | 1.5 | ceteareth-25 |
| Glycerol monostearate s.e. | 5.0 | glyceryl stearate |
| Uvinul MS 40 | 0.5 | benzophenone-4 |
| Paraffin oil | 3.5 | paraffin oil |
| Cetyl alcohol | 0.5 | cetyl alcohol |
| Luvitol EHO | 10.0 | cetearyl octanoate |
| D-Panthenol 50P | 3.0 | panthenol and propylene glycol |
| Vitamin E acetate | 1.0 | tocopheryl acetate |
| Tegiloxan 100 | 0.3 | dimethicone |
| Nip-Nip | 0.1 | methyl and propyl 4-hydroxy-benzoate (7:3) |

34

-continued

| Water phase: | [%] | |
|---|---|---|
| Polymer No. 4, 12, 17, 18, 20, 24-28, 33-34, 38-48, 55-56, (30% strength aqueous solution) | 1.5 | |
| Water | 70.0 | |
| 1,2-Propylene glycol | 1.5 | |
| Germall II | 0.1 | imidazolidinyl-urea |

Preparation: weigh in and, with stirring, homogenize the oil phase and the aqueous phase separately at a temperature of 80° C. Slowly stir the water phase into the oil phase. Slowly cool to room temperature with stirring.

We claim:

1. A copolymer A), obtained by free-radical copolymerization of:
    a) 20 to 40% by weight of methacrylamide,
    b) 40 to 70% by weight of vinylpyrrolidone and/or vinylcaprolactam, and
    c) 0.2 to 25% by weight of vinylimidazole and/or derivatives thereof,
    in the presence of from 1 to 20% by weight of polymers d2) which have at least 50% by weight repeat units derived from vinyl alcohol and/or starch and starch derivatives d3),
    wherein the copolymer provides a tack-free smooth film.

2. A cosmetic composition, comprising the copolymer of claim 1 and at least one at least one cosmetically acceptable carrier.

3. The cosmetic composition of claim 2, which is a skin-cleansing composition, a composition for the care and protection of the skin, a nail care composition, a preparation for decorative cosmetics, a hair-treatment composition or a coating composition.

4. A copolymer A), obtained by free-radical copolymerization of:
    a) 10 to 45% by weight, based on the total weight of components a) to d), of acrylamide and/or methacrylamide,
    b) 60 to 90% by weight, based on the total weight of components a) to d), of vinylpyrrolidone and/or vinylcaprolactam, and
    c) 0.2 to 25% by weight, based on the total weight of components a) to d), of vinylimidazole and/or derivatives thereof, optionally in the presence of up to 25% by weight, based on the total weight of components a) to d), of at least one water-soluble component d), which is selected from the group consisting of:
        d1) polyether-containing compounds,
        d2) polymers which have at least 50% by weight repeat units derived from vinyl alcohol,
        d3) starch and starch derivatives,
            and mixtures thereof,
    wherein the copolymer provides a tack-free smooth film.

5. The copolymer A) as claimed in claim 4 obtained by free-radical copolymerization of:
    a) 10 to 45% by weight, based on the total weight of components a) to d), of methacrylamide,
    b) 60 to 90% by weight, based on the total weight of components a) to d), of vinylpyrrolidone and/or vinylcaprolactam, and
    c) 0.2 to 25% by weight, based on the total weight of components a) to d), of vinylimidazole and/or derivatives thereof, optionally, in the presence of up to 20% by weight, based on the total weight of components a) to d), of polymers d2) and/or starch and starch derivatives d3).

6. A copolymer A), obtained by free-radical copolymerization of:
   a) 20 to 40% by weight, based on the total weight of components a) to d), of acrylamide and/or methacrylamide,
   b) 40 to 70% by weight, based on the total weight of components a) to d), of vinylpyrrolidone and/or vinylcaprolactam, and
   c) 0.2 to 25% by weight, based on the total weight of components a) to d), of vinylimidazole and derivatives thereof,
   optionally in the presence of up to 25% by weight, based on the total weight of components a) to d), of at least one water-soluble component d), which is selected from the group consisting of:
      d1) polyether-containing compounds,
      d2) polymers which have at least 50% by weight repeat units derived from vinyl alcohol,
      d3) starch and starch derivatives,
      and mixtures thereof,
   wherein the copolymer provides a tack-free smooth film.

7. The copolymer A) as claimed in claim 6, obtained by free-radical polymerization of:
   a) 20 to 40% by weight of methacrylamide,
   b) 40 to 70% by weight of vinylpyrrolidone and/or vinylcaprolactam, and
   c) 1 to 20% by weight of vinylimidazole and derivatives thereof.

8. A copolymer A), obtained by free-radical copolymerization of:
   a) 5 to 50% by weight, based on the total weight of components a) to d), of acrylamide and/or methacrylamide,
   b) 40 to 85% by weight, based on the total weight of components a) to d), of vinylpyrrolidone and/or vinylcaprolactam, and
   c) 0.2 to 25% by weight, based on the total weight of components a) to d), of vinylimidazole and derivatives thereof,
   optionally in the presence of up to 25% by weight, based on the total weight of components a) to d), of at least one water-soluble component d), which is selected from the group consisting of:
      d1) polyether-containing compounds,
      d2) polymers which have at least 50% by weight repeat units derived from vinyl alcohol,
      d3) starch and starch derivatives,
      and mixtures thereof,
   wherein the copolymer provides a tack-free smooth film.

9. The copolymer A) as claimed in claim 8, obtained by free-radical copolymerization of:
   a) 5 to 50% by weight, based on the total weight of components a) to d), of methacrylamide,
   b) 40 to 85% by weight, based on the total weight of components a) to d), of vinylpyrrolidone and/or vinylcaprolactam, and
   c) 0.2 to 20% by weight, based on the total weight of components a) to d), of vinylimidazole and/or derivatives thereof,
   optionally in the presence of up to 10% by weight, based on the total weight of components a) to d), of polymers d2), which are derived from vinyl alcohol, and optionally in the presence of up to 1% by weight, based on the total weight of components a) to d), of at least one crosslinker.

10. A copolymer A), obtained by free-radical copolymerization of:
    a) 30 to 40% by weight, based on the total weight of components a) to d), of methacrylamide,
    b) 20 to 60% by weight, based on the total weight of components a) to d), of vinylpyrrolidone and 1 to 20% by weight of vinylcaprolactam, and
    c) 0.2 to 25% by weight, based on the total weight of components a) to d), of vinylimidazole and/or derivatives thereof,
    optionally in the presence of up to 25% by weight, based on the total weight of components a) to d), of at least one water-soluble component d), which is selected from the group consisting of:
       d1) polyether-containing compounds,
       d2) polymers which have at least 50% by weight repeat units derived from vinyl alcohol,
       d3) starch and starch derivatives,
       and mixtures thereof,
    wherein the copolymer provides a tack-free smooth film.

11. The copolymer A) as claimed in claim 8, obtained by free-radical polymerization of:
    a) 7 to 45% by weight of methacrylamide,
    b) 50 to 80% by weight of vinylpyrrolidone and/or vinylcaprolactam, and
    c) 0.3 to 10% by weight of vinylimidazole and/or derivatives thereof, in the presence of 0.1 to 10% by weight of polymers d2) which are derived from vinyl alcohol.

12. The copolymer A) as claimed in claim 8, obtained by free-radical polymerization of:
    a) 10 to 45% by weight of methacrylamide,
    b) 50 to 80% by weight of vinylpyrrolidone and/or vinylcaprolactam, and
    c) 0.3 to 10% by weight of vinylimidazole and/or a derivative thereof.

13. The copolymer A) as claimed in claim 8, obtained by free-radical polymerization of:
    a) 10 to 45% by weight of methacrylamide,
    b) 50 to 80% by weight of vinylpyrrolidone and/or vinylcaprolactam, and
    c) 0.5 to 5% by weight of vinylimidazole and/or derivatives thereof.

14. A process for the preparation of copolymer A), as claimed in claim 5, by free-radical polymerization of the monomers a) with at least one further monomer chosen from the monomers b) and c), optionally in the presence of up to 25% by weight, based on the total weight of components a) to b), of a water-soluble component d), wherein the polymerization is carried out in an aqueous solvent.

15. The process as claimed in claim 14, wherein the polymerization is carried out at a pH in the range from 6 to 8.

16. The process as claimed in claim 15, wherein the polymerization is carried out at a pH in the range from 6.4 to 7.4.

17. A method of coating a substrate, comprising applying the copolymer as claimed in claim 5 to a substrate.

18. The method as claimed in claim 17, wherein the substrate comprises a solid medicament, a textile, paper, a printable source or leather.

19. A method of making a pharmaceutical composition, comprising adding the copolymer, as claimed in claim 5, as an auxiliary, to one or more pharmaceutical components.

20. A method of making a composition, comprising contacting the copolymer A), as claimed in claim 5, with one or more additives.

* * * * *